United States Patent [19]
Epstein et al.

[11] Patent Number: 6,022,361
[45] Date of Patent: Feb. 8, 2000

[54] DEVICE FOR INTRODUCING AND POLYMERIZING POLYMERIC BIOMATERIALS IN THE HUMAN BODY AND METHOD

[75] Inventors: Gordon H. Epstein; David M. Taylor, both of Fremont; Philip P. Corso, Jr., Dublin, all of Calif.

[73] Assignee: Biointerventional Corporation, Pleasanton, Calif.

[21] Appl. No.: 09/169,219

[22] Filed: Oct. 9, 1998

[51] Int. Cl.$^7$ .................................................. A61B 17/00
[52] U.S. Cl. ............................................. 606/151; 606/213
[58] Field of Search ................................. 606/213, 215, 606/151, 194; 128/898, 899; 604/101

[56] References Cited

U.S. PATENT DOCUMENTS

| | | | |
|---|---|---|---|
| 5,258,000 | 11/1993 | Gianturco | 606/151 |
| 5,328,471 | 7/1994 | Slepian . | |
| 5,410,016 | 4/1995 | Hubbell et al. . | |
| 5,468,505 | 11/1995 | Hubbell et al. . | |
| 5,529,914 | 6/1996 | Hubbell et al. . | |
| 5,573,934 | 11/1996 | Hubbell et al. . | |
| 5,612,050 | 3/1997 | Rowe et al. . | |

*Primary Examiner*—Michael Buiz
*Assistant Examiner*—Vikki Trinh
*Attorney, Agent, or Firm*—Flehr Hohbach Test Albritton & Herbert

[57] ABSTRACT

A device for introducing and polymerizing polymeric biomaterials in the human body. The device has a first elongate tubular member having proximal and distal extremities and a longitudinal axis. An expansile member is carried by the distal extremity of the first elongate tubular member and is movable between contracted and expanded positions. The expansile member has a predetermined configuration in the expanded position. A deformable membrane covers the expansile member and is sized so as to be capable of overlying and underlying the expansile member in the expanded position. A second elongate tubular member has proximal and distal extremities, a longitudinal axis and a first lumen extending from the proximal to the distal extremity of the second elongate tubular member. The distal extremity of said second elongate tubular member terminates proximal to the distal extremity of said first elongate tubular member and adjacent to said expansile member. The first elongate tubular member is carried by said second elongate tubular member. Light conductors are carried by the second elongate tubular member for conducting light to the distal extremity of the second elongate tubular member.

8 Claims, 2 Drawing Sheets

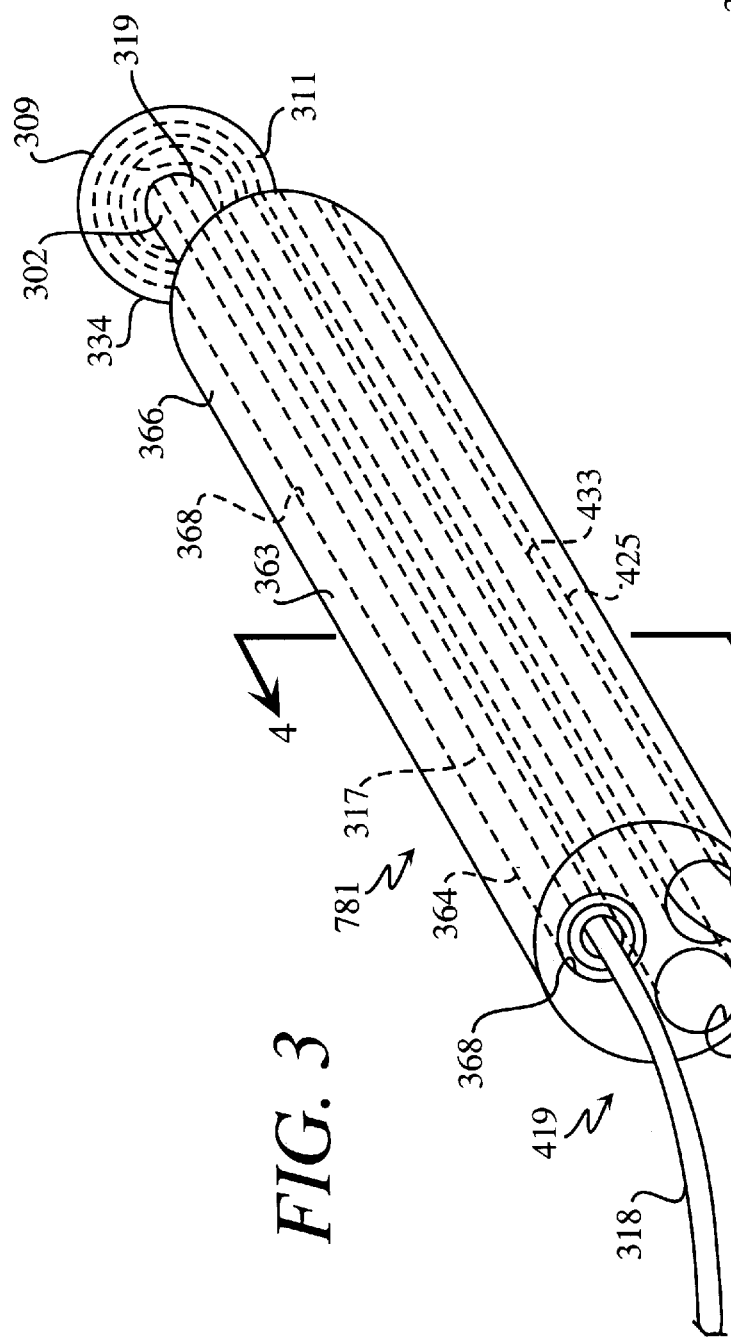
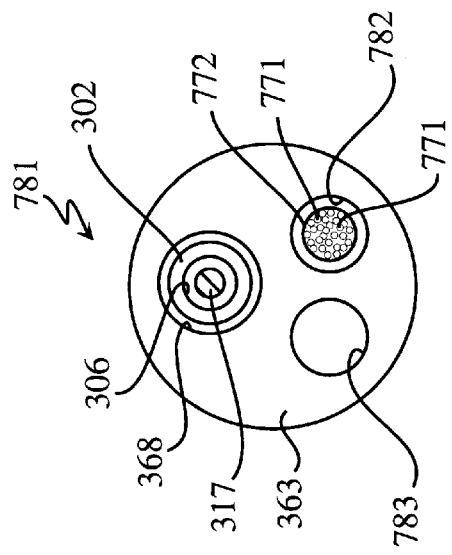

DEVICE FOR INTRODUCING AND POLYMERIZING POLYMERIC BIOMATERIALS IN THE HUMAN BODY AND METHOD

This invention relates to a device and system for introducing and polymerizing polymeric biomaterials, particularly hydropolymers or hydrogels, in the human body and method for using the same.

Polymeric biomaterials may be introduced into the human body for a number of applications including the prevention of post-operative tissue adhesions, as biological sealants, as drug delivery carriers and for other therapeutic interventions. In particular, photopolymerizable, biodegradable hydrogel polymers for use as tissue sealants and adhesives have been disclosed in U.S. Pat. Nos. 5,410,016; 5,573,934 and 5,612,050. Such polymers are applied or introduced into the human body at preferred sites of action and are then exposed to light and/or thermal energy whereupon polymerization occurs.

U.S. Pat. No. 5,782,860, issued Jul. 21, 1998, and U.S. Application Ser. No. 08/126,963, filed Jul. 31 1998, the relevant portions of which are hereby incorporated by reference in their entirety, disclose devices and methods for percutaneously occluding puncture sites and tracts in the human body and introducing biological sealants in conjunction therewith.

There is a need for a device and system for percutaneous access and occlusion of vascular access sites and other puncture sites and natural tracts in the human body which utilize photopolymerizable hydrogel polymers as biological sealants in conjunction therewith.

In general it is an object of the present invention to provide a device and method for use in the percutaneous introduction and polymerization of polymerizable hydrogel polymers into the body.

Another object of the invention is to provide a device and method of the above character for percutaneous occlusion of vascular access sites in conjunction with which a biological sealant in the form of photopolymerizable hydrogel polymers is utilized.

Another object of the invention is to provide a device of the above character which provides means for conducting light energy to the site in a puncture at which the polymer is deposited in order to photopolymerize the polymer.

Another object of the invention is to provide a device of the above character which provides means for fiber-optically conducting light energy to the site in a puncture at which the polymer is deposited in order to photopolymerize the polymer.

Another object is to provide a device of the above character which is quick, safe, easy to use and is disposable.

Additional objects and features of the invention will appear from the following description in which the preferred embodiments and the methods using the same are described in conjunction with the accompanying drawings.

FIG. 3 is an isometric view of another embodiment of a device for introducing and polymerizing polymeric biomaterials incorporating the present invention.

FIG. 4 is a sectional view taken along the line 4—4 of FIG. 3.

In general, the device of the present invention for introducing and polymerizing polymeric biomaterials in the human body has a first elongate tubular member having proximal and distal extremities and a longitudinal axis. An expansile member is carried by the distal extremity of the first elongate tubular member and is movable between contracted and expanded positions. The expansile member has a predetermined configuration in the expanded position. A deformable membrane covers the expansile member and is sized so as to be capable of overlying and underlying the expansile member in the expanded position. Deployment means are carried by the proximal extremity of the first elongate tubular member and are adapted to be operated by the human hand for controlling movement of the expansile member between the contracted and expanded positions. A second elongate tubular member has proximal and distal extremities, a longitudinal axis and a first lumen extending from the proximal to the distal extremity of the second elongate tubular member. The distal extremity of said second elongate tubular member terminates proximal to the distal extremity of said first elongate tubular member and adjacent to said expansile member. The first elongate tubular member is carried by said second elongate tubular member. Means are connected to said second elongate tubular member for introducing a polymeric biomaterial into the body proximal to the expansile member and distal to the second elongate tubular member. Means are carried by the second elongate tubular member for conducting light to the distal extremity of the second elongate tubular member.

Figure 1:
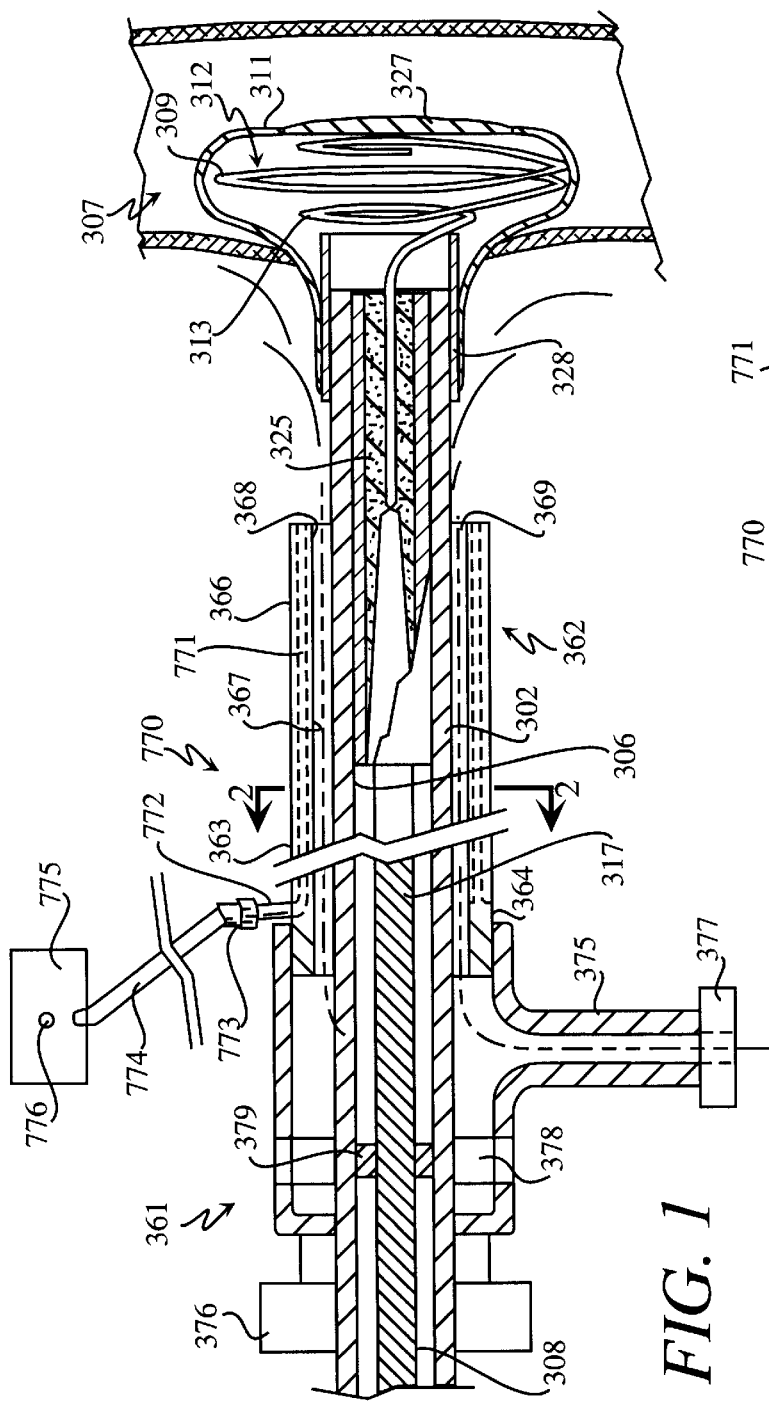
FIG. 1 is a cross-sectional view of a device for introducing and polymerizing polymeric biomaterials in the human body incorporating the present invention.
Figure 2:
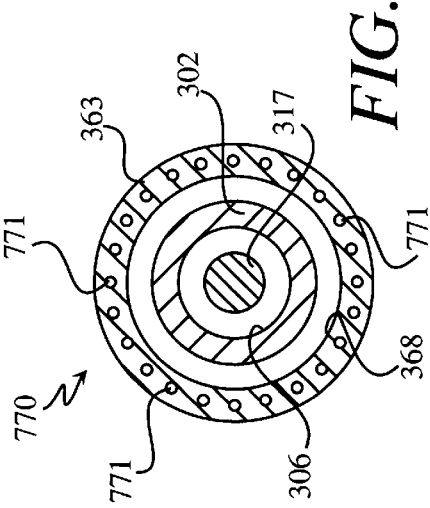
FIG. 2 is a sectional view taken along the line 2—2 of FIG. 1.

More specifically, as shown in FIGS. 1–2, the device 770 of the present invention is very similar to that shown in FIG. 24 of U.S. Application Ser. No. 08/126,963 with the principal difference being that, in addition, it provides means carried by the second elongate tubular member for conducting light, preferably fiberoptically, to the distal extremity of the second elongate tubular member in order to photopolymerize a hydrogel polymer sealant that has been deposited proximal to the expansile member and external to the vessel lumen. Thus all parts of the device 301 that are present in the device 770 carry the same numbers. The fiber optic conducting means 771 comprises conventional fiber optic conductors or fibers 771, preferably a plurality or bundle of fibers, which are circumferentially embedded in the extruded second elongate tubular member 363 and which extend from the proximal 364 to the distal extremity 366 of the second elongate tubular member 363.

The fiber optic conductors 771 are constructed of a suitable material, such as plastic or glass, and are of a suitable size as is conventional in the art. The fibers 771 are of a suitable length so that they extend distally to terminate at the distal-most end of the distal extremity 366 of the second elongate tubular member 363 thereby illuminating an area immediately distal and adjacent thereto as hereinafter described. The fiber optic conductors 771 extend proximally, into the proximal extremity 364 of the second elongate tubular member 363, whence they exit. Alternatively, the fiber optic conductors 771 can extend further proximally into the body of the tee adaptor 375, exiting therefrom. The proximal portions 772 of the fiber optic conductors 771 extending out of the second elongate tubular member 363 are conjoined or bundled and provided with a fitting 773 capable of being operatively connected to an optical connector cable 774 which is connected to a light source 775 controlled by a switch 776. The light source 775 is selected to provide actinic light of an appropriate wavelength and intensity so as to be capable of successfully polymerizing a hydrogel sealant, as hereinbefore described, within a predetermined period of time. Preferably, the light has a wavelength corresponding to ultraviolet light but may be in a plurality of ranges, including the visible or laser ranges as well.

In addition, in order to optimize flow of a hydrogel sealant, the inner wall 367 of the second elongate tubular member 363 can be conventionally coated with an appropriate material, as for example, a hydrophilic material, to increase the lubriciousness thereof.

Operation and use of the device 770 is similar to that described for the device 301 except for the ability to introduce, and thereafter polymerize, hydrogel sealants by fiber-optically conducting and delivering light to the sealants with the device 770. After the sealant has been introduced into the proximal end 364 of the second elongate tubular member 363 it exits proximal to the distal extremity 304 of the first flexible elongate tubular member 302 and adjacent to the expansile mechanism 309 as described in U.S. Application Ser. No. 08/126,963. The fitting 773 connected to the conjoined fiber optic bundle 772 is connected to the optical connector cable 774 leading to the light source 775. It should be appreciated that this connection may be made prior to introduction of the hydrogel. The switch 776 on the light source 775 is placed in the on position for a predetermined period of time, based upon the hydrogel being utilized, and the hydrogel polymer is thereby irradiated until it polymerizes as disclosed in the U.S. patents hereinbefore discussed. The remainder of the operation of the device 770 is as described in conjunction with the use of the device 360 in the aforementioned patent application.

Another embodiment of the device for introducing and polymerizing polymeric biomaterials incorporating the present invention is shown in FIGS. 3–4. The device 781 is very similar to that shown in FIG. 27 of U.S. Application Ser. No. 08/126,963 with the principal differences being that the second elongate tubular member 363 of device 781 is provided with second and third lumens 782 and 783 and there is no third elongate tubular member associated therewith. Thus, all parts of the device 418 that are present in the device 781 carry the same numbers.

The second 782 and third 783 lumens have appropriate shapes, preferably being circular in cross-section, and extend from the proximal extremity 364 to the distal extremity 366 of the second elongate tubular member 363. Both second and third lumens 782 and 783 are of appropriate diameters, preferably slightly smaller in diameter than the first lumen 368 of the second elongate tubular member 363. The third lumen 783 may be utilized for sealant introduction as hereinbefore described in U.S. Application Ser. No. 08/126,963. The second lumen 782 carries fiber optic conductors 771, preferably a conjoined bundle 772 thereof, the conductors 771 extending proximally, from the distal tip of the distal extremity 366 to the proximal extremity 364 of the second elongate tubular member 363 whence the bundle 772 extends out of the second elongate tubular member 363. The fiberoptic conductors 771 are formed as hereinbefore discussed in conjunction with device 770 and are, preferably, fixed in position within the second elongate tubular member 363 by appropriate means, as for example by adhesive bonding thereto. The remainder of the fiber optic apparatus, including the fitting 773, cable 774 and light source 775 are also as hereinbefore discussed.

Operation and use of the device 781 is similar to that hereinbefore described for device 770.

In additional embodiments, as hereinafter described, the second elongate tubular members of devices 770 and 781 are formed of a clear, preferably transparent, suitable plastic material such as Pebax™. Alternatively, just the distal extremities of the second elongate tubular members are transparently formed or proximal portions of the clear second elongate tubular members may be made opaque by any appropriate means, as, for example, by coating, leaving transparent distal portions. It should also be appreciated that the fiberoptic conductors can be provided with cladding which has been made opaque throughout similar proximal portions to achieve similar results. In these embodiments conventional side emitting fiber optic conductors, which are known in the art, are employed so that conducted light is emitted along the lengths thereof and through the transparent portions of the second elongate tubular members. In this manner more light may be diffusely transmitted to photo-polymerizable agents, facilitating polymerization.

It should also be appreciated that the device and method of the present invention are not limited to use with photo-polymerizable sealants nor are they limited to use in percutaneously occluding vascular puncture sites. For example, alternate forms of energy can be applied by various embodiments in which the fiber optic conducting bundles are replaced by wires. As such, radio-frequency energy or heat energy can be conducted to the distal extremity of the second elongate tubular member. This broadens the scope, and thus the type, of the polymers that can be utilized as sealants and polymerized in situ.

In addition, anti-adhesive agents, antibiotics and other drugs can be carried and delivered by polymerizable biomaterials, to any organ or structure which is percutaneously accessible and for which therapeutic intervention is required, where such therapy can be accomplished by occluding a portion of the organ or structure and subsequently introducing a compound proximal to the occlusion. As such, a number of therapeutic interventions can be achieved in conjunction with the use of the expansile device of the present invention.

In particular, the accurate, percutaneous delivery of a biological sealant into a puncture site followed by photo-activation thereof provides a novel means of percutaneously occluding vascular access sites while simultaneously affording the opportunity to deposit additional therapeutic agents thereto.

What is claimed:

1. A device for introducing and polymerizing polymeric biomaterials in the human body comprising a first elongate tubular member having proximal and distal extremities and having a longitudinal axis, an expansile member carried by the distal extremity of the first elongate tubular member and movable between contracted and expanded positions, said expansile member having a predetermined configuration in the expanded position, a deformable membrane covering the expansile member, said deformable membrane being sized so as to be capable of overlying and underlying the expansile member in the expanded position, deployment means carried by the proximal extremity of the first elongate tubular member and adapted to be operated by the human hand for controlling movement of the expansile member between the contracted and expanded positions, a second elongate tubular member having proximal and distal extremities, a longitudinal axis and a first lumen extending from the proximal to the distal extremity of the second elongate tubular member, the distal extremity of said second elongate tubular member terminating proximal to the distal extremity of said first elongate tubular member and adjacent to said expansile member, said first elongate tubular member being carried by said second elongate tubular member, means connected to said second elongate tubular member for introducing a polymeric biomaterial into the body proximal to said expansile member and distal to the second elongate tubular member and means carried by said second elongate tubular member for conducting light to the distal extremity of said second elongate tubular member.

2. A device for expansion within a blood vessel having a wall defining a lumen in the body comprising a first elongate tubular member having proximal and distal extremities and having a longitudinal axis, an expansile member carried by the distal extremity of the first elongate tubular member and movable between contracted and expanded positions, said expansile member having a predetermined configuration in the expanded position, a deformable membrane covering the expansile member, said deformable membrane being sized so as to be capable of overlying and underlying the expansile member in the expanded position, deployment means carried by the proximal extremity of the first elongate tubular member and adapted to be operated by the human hand for controlling movement of the expansile member between the contracted and expanded positions, a second elongate tubular member having proximal and distal extremities, a longitudinal axis and a first lumen extending from the proximal to the distal extremity of the second elongate tubular member, the distal extremity of said second elongate tubular member terminating proximal to the distal extremity of said first elongate tubular member and adjacent to said expansile member, said first elongate tubular member being carried by said second elongate tubular member, means connected to said second elongate tubular member for introducing a polymeric biomaterial into the body proximal to said expansile member and external to the lumen of the vessel and means carried by said second elongate tubular member for conducting light to the distal extremity of said second elongate tubular member.

3. A device as in claim 2 wherein said light conducting means includes fiber optic conductors.

4. A device as in claim 3 wherein said fiber optic conductors are embedded in the second elongate tubular member.

5. A device as in claim 3 wherein the second elongate tubular member has a second lumen extending from the proximal to the distal extremity of the second elongate tubular member and said fiber optic conductors are carried in said second lumen.

6. A device as in claim 3 wherein at least a portion of said second elongate tubular member is transparent.

7. A device as in claim 5 wherein the second elongate tubular member has a third lumen extending from the proximal to the distal extremity of the second elongate tubular member.

8. A method for introducing and polymerizing a polymeric biomaterial in a structure in the human body having a portion capable of being occluded by use of a device having a first elongate tubular member having proximal and distal extremities and having a longitudinal axis, an expansile member carried by the distal extremity of the first elongate tubular member and movable between contracted and expanded positions, said expansile member having a predetermined configuration in the expanded position, a deformable membrane covering the expansile member, said deformable membrane being sized so as to be capable of overlying and underlying the expansile member in the expanded position, deployment means carried by the proximal extremity of the first elongate tubular member and adapted to be operated by the human hand for controlling movement of the expansile member between the contracted and expanded positions, a second elongate tubular member having proximal and distal extremities, a longitudinal axis and a first lumen extending from the proximal to the distal extremity of the second elongate tubular member, the distal extremity of said second elongate tubular member terminating proximal to the distal extremity of said first elongate tubular member and adjacent to said expansile member, said first elongate tubular member being carried by said second elongate tubular member, means connected to said second elongate tubular member for introducing a polymeric biomaterial into the body proximal to said expansile member and means carried by said second elongate tubular member for conducting light to the distal extremity of said second elongate tubular member, the method comprising the steps of introducing the distal extremity of the first elongate tubular member carrying the expansile member into the portion of the structure in the body capable of being occluded, moving the expansile member from the contracted to the expanded position, pulling the expansile member in the expanded position proximally to occlude the portion of the structure capable of being occluded, introducing a polymeric biomaterial into the body proximal to the expansile member and proximal to the portion of the structure occluded and thereafter conducting light to the distal extremity of the second elongate tubular member in order to polymerize the biomaterial.

* * * * *